United States Patent [19]

Brantigan

[11] 4,016,863
[45] Apr. 12, 1977

[54] TISSUE TONOMETER DEVICE FOR USE IN MEASURING GAS IN BODY TISSUE

[76] Inventor: John W. Brantigan, 7723 Forest Drive, NE., Seattle, Wash. 98115

[22] Filed: Aug. 27, 1975

[21] Appl. No.: 608,157

[52] U.S. Cl. .............................. 128/2 G; 128/2 L
[51] Int. Cl.² ............................................ A61B 5/00
[58] Field of Search ....... 128/2 E, 2 G, 2 L, 214 R, 128/348

[56] References Cited

UNITED STATES PATENTS

| 3,572,315 | 3/1971 | Cullen | 128/2 E |
|---|---|---|---|
| 3,658,053 | 4/1972 | Fergusson et al. | 128/2 E X |
| 3,824,157 | 7/1974 | Macur | 128/2 E |
| 3,844,275 | 10/1974 | Elliott | 128/2 E |
| 3,893,448 | 7/1975 | Brantigan | 128/2 G |
| 3,923,627 | 12/1975 | Niedrach et al. | 128/2 E X |

FOREIGN PATENTS OR APPLICATIONS

| 259,722 | 11/1964 | Australia | 128/2 E |
| 994,077 | 6/1965 | United Kingdom | 128/2 E |

OTHER PUBLICATIONS

Wald, A., et al., *Med. & Biol. Engng.*, vol. 8, No. 2, pp. 111-128, 1970.

Primary Examiner—Kyle L. Howell
Attorney, Agent, or Firm—Hill, Gross, Simpson, Van Santen, Steadman, Chiara & Simpson

[57] ABSTRACT

A tissue gas diffusion catheter device which includes an impervious catheter, the lumen of which is filled with an impervious element extending beyond the distal end of the catheter. The catheter is enclosed for its full length as well as the element extending through the lumen of the catheter and there beyond to a plug of the same diameter as the catheter by means of a membrane permeable to gases but not to liquids that might be found in body tissue. That end portion between the distal termination of the catheter and the plug forms a liquid chamber which may be filled with water or other suitable fluid in a manner to allow the catheter fluid to become equilibrated or "tonometered" with the gas contained in the surrounding body tissue, such tonometer fluid being capable of being analyzed for gas content using the usual blood gas analyzing instruments available in hospital laboratories. Such analysis may be made in an immediately accessible laboratory or a laboratory remotely located.

10 Claims, 6 Drawing Figures

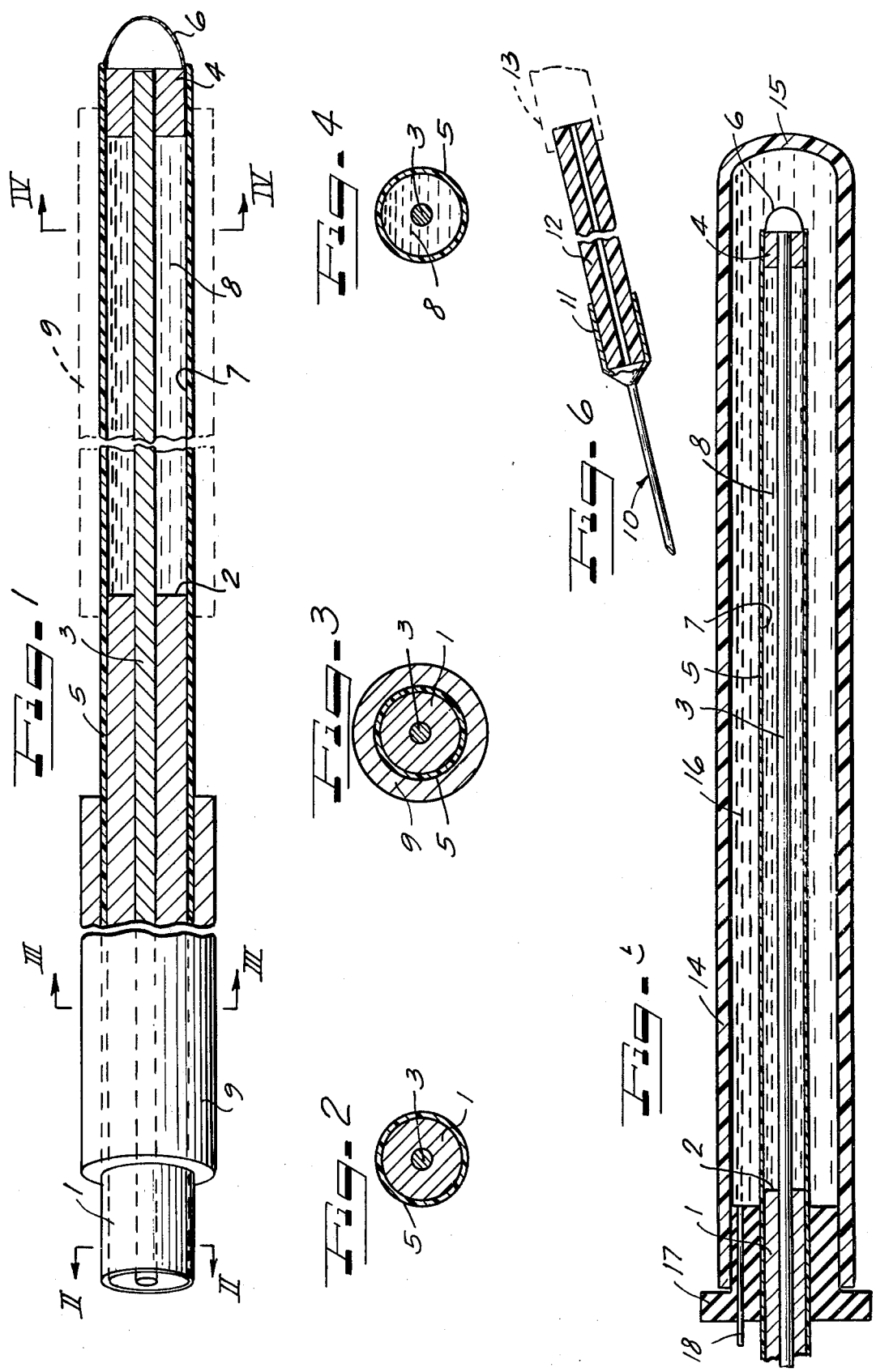

TISSUE TONOMETER DEVICE FOR USE IN MEASURING GAS IN BODY TISSUE

BRIEF SUMMARY OF THE INVENTION

There are many clinical situations in which the delivery of oxygen to a patient's tissue is in doubt and in which measurement of the exact oxygen and carbon dioxide levels might provide decisive information determining optimum therapy.

Heretofore, tissue gases have been measured by subcutaneous gas pockets, by a perfusion type of tissue tonometer, and by a diffusion-catheter-mass spectrometer combination.

In the subcutaneous gas pocket method a large volume of air, approximately 30 cc. is injected beneath the skin. Over a period of hours the air becomes equilibrated with the gas dissolved in tissue fluid, and samples of the equilibrated air are aspirated and analyzed by standard instruments. This method is limited to tissue areas that can tolerate injections of the large bolus of air and has not been used clinically.

In the perfusion type of tissue tonometer a 10 cm. length of silastic tubing is implanted beneath the skin with both ends of the tubing penetrating the skin through separate puncture wounds. A water solution is pumped through this tubing at a sufficiently slow rate to allow the water to become equilibrated with tissue gases. The exiting fluid is conducted in a continuous flow to the inlet of a standard clinical blood gas instrument at the bedside, and the gas content analyzed. This tissue tonometer is limited to locations that permit a 10 cm. implant with both exit and entry wounds, and in practice, only subcutaneous measurements can be made, as areas such as the muscle compartments are inaccessible to this approach. Further, this technique requires that an expensive blood gas analyzing instrument be at the bedside and be devoted exclusively to one patient. In addition, it should be noted that it is highly difficult to properly advance a silastic catheter through tissue from one wound opening to another.

As mentioned above, tissue gases have been measured in both research and clinical applications with a mass spectrometer analyzing tissue gases sampled by vacuum suction through a diffusion membrane catheter. The catheters are of small size, require only a single puncture, and can be used in areas difficult of access such as the heart. While this method is highly accurate, it requires a mass spectrometer, a very expensive electronic analyzing instrument that is unavailable to many hospitals.

The instant catheter device applies the diffusion principle in a unique way that allows a small volume of fluid to be introduced through a single narrow-gauge puncture and to be equilibrated with the gas dissolved in the tissue, allowing the tonometered fluid to be removed for remote laboratory analysis. In this manner the instant invention has achieved the desirable goal of overcoming the disadvantages of the above described structures and allowing individual discrete determinations of tissue gases to be made with a minimum of tissue trauma utilizing blood gas analyzing equipment ordinarily available in hospital laboratories. For example, the instant invention is highly desirable for treatment of the so-called "compartment syndrome" in orthopedics in which the swelling following a lower leg fracture cuts off the blood supply to the muscles. The only early symptom is pain and that is certainly difficult to interpret in a fracture. Compartment syndrome occurs to some degree in up to 20% of lower leg fractures causing loss of various nerve and muscle function and treatment requires disfiguring surgery and is not casually used. The catheter device embodied in this invention will allow measurement of tissue oxygen, and thus diagnosis of blood supply to muscle in compartment syndrome, without a mass spectrometer and will be available to anyone having a hospital blood gas instrument.

The instant invention embodies a known form of small diameter catheter, with a liquid and gas impermeable element extending through the lumen thereof and beyond the end of the catheter to terminate in a plug of the same outside diameter as the catheter itself thereby establishing a space between the terminal end of the catheter and the plug. The catheter and such space and plug are covered completely by a membrane of material permeable to body gases such as oxygen, carbon dioxide, nitrogen, argon, helium, anesthetic agents, inter alia. This tubular membrane is tipped to affect a seal around the distal face of the plug and distal end of the membrane. The chamber is thereby formed around the impermeable element between it and the membrane, which chamber is initially filled with water or an equivalent liquid into which gas in the tissue may pass by diffusion through the membrane. The entire device may be made in a small diameter and the chamber having various capacities as may be deemed desirable for different types or structures of analyzing instruments. The device allows a volume of fluid to be introduced with a minimum of trauma into areas of body tissue that are difficult of access and the fluid can become equilibrated or tonometered with the gases in the tissue fluid and be removed for remote analysis as a measure of the gas tensions present in the tissue. Means are also provided that are impermeable to gas to cover that portion of the device containing the chamber and protect the tonometered fluid until it is removed for analyzation immediately, or at a later time, and in a different location to which it may be transported.

The instant invention achieves advantages therefor over existing methods and devices in allowing measurements of tissue gases without requiring expensive supplemental electronic equipment not available in most hospitals, which requires only a single entry puncture, and makes measurements possible in areas inaccessible to measurement with previous economical devices to provide a quantity of tonometered liquid for analysis by blood gas analyzing apparatus available in most hospitals. Other objects, features and advantages of the invention will be readily apparent from the following description of a preferred embodiment thereof, taken in conjunction with the accompanying drawing, although variations and modifications may be effected without departing from the spirit and scope of the novel concepts of the disclosure.

BRIEF DESCRIPTION OF THE DRAWING

FIG. 1 is a fragmentary part sectional part elevational view of a device embodying improvements of the instant invention.

FIG. 2 is a vertical sectional view taken substantially as indicated by the line II—II of FIG. 1 looking in the direction of the arrows;

FIG. 3 is a vertical sectional view taken substantially as indicated by the line III—III of FIG. 1;

FIG. 4 is a sectional view taken substantially as indicated by the line IV—IV of FIG. 1;

FIG. 5 is a fragmentary vertical sectional view through the apparatus showing the use of a different form of protector for the tonometered liquid to analysis thereof; and FIG. 6 illustrating the use of a hypodermic needle through which the tonometered fluid may be removed directly to an apparatus for analysis.

DETAILED DESCRIPTION

All figures of the drawing are greatly exaggerated for purposes of better illustrating the invention.

In the first illustrated embodiment of the instant invention as seen in FIGS. 1–4, there is shown a catheter 1, preferably of stainless steel or equivalent tubing which terminates at its distal end at point 2 which is short of the entire length of the catheter device. The lumen of the catheter is plugged by an elongated element 3 which extends beyond the distal end of the catheter 1 and terminates in a plug 4 of the same outside diameter as the catheter 1. This elongated element 3 is preferably a solid rod or wire so as to provide the maximum structural support in the smallest volume, although it is noted that stainless steel needle tubing might have sufficient strength to perform the function and the material might be more readily available in the desired size on the market for manufacturing purposes. In that event if the element 3 is tubular, it must be plugged to prevent leakage. At least the distal end portion, if not the entire length of the catheter 1, is covered by a membrane 5 of silicone rubber, "Teflon" and closed at its distal end by a sealed distal tip 6 which can be made of a material, such as a "Teflon-FEP" monofilament (the words in quotation marks being trademarks of DuPont, E. I. de Nemours & Co., Inc.). Other equivalent materials may be utilized for the membrane 5 and its tip 6 as long as the material is permeable to gases, not liquids, found in the body and which are to be sampled and analyzed.

From the showing in FIG. 1 it will be seen that beyond the distal end of the catheter and to the plug 4 made of equivalent material to the catheter, the membrane 5 establishes an annular chamber 7 around the elongated element 3 which chamber is filled with water 8 or other liquids suitable for tonometry of gases. In manufacture, the chamber 7 may be filled with water before the tubular membrane 3 is sealed at the end by the tip 6 and before the plug 4 is added. The entire end may have to be briefly immersed in water or other fluid while part 4 is positioned and the monofilament 6 inserted within the tubular membrane 5 is inserted in the membrane and secured thereto. Since the tip monofilament 6 expands when heated, it can be sealed within the tubular membrane 5 by heat molding or heat welding to form the final sealed end of the catheter device. This procedure would prevent air bubbles and should present little, if any, difficulty in practice. A catheter device is then ready for use.

In use, the catheter device may be inserted to a desired point within the body of a patient by catheter insertion devices known in the art, by use of a cannulated needle, closed or split lengthwise to a satisfactory degree, by slanting the end of the plug 4 to provide a point thereon and using a tightly fitted monofilament over the end thereof as suggested in Brantigan U.S. Pat. No. 3,893,448 dated July 8, 1975 or in a preformed entry, inter alia, depending upon the surgeon's desire.

Gases contained in the surrounding body tissue permeate through the membrane 5 so that the fluid 8 inside the chamber 7 becomes equilibrated or tonometered with the tissue gases. The time required for equilibration varies somewhat for various membrane materials but is in the general range of 10 minutes. After the catheter device has been in tissue for this period of time, the catheter is removed from tissue and immediately placed within a means for sealing off that portion of the membrane 5 surrounding the chamber 7 by means impermeable to gas to protect the diffusing membrane and tonometered fluid from exposure to outside air during transportation to the hospital laboratory or other location where the analysis is made.

In the case of FIGS. 1 and 3, the protective means is in the form of a gas impervious sleeve 9 embracing the tubular membrane 5 and is in an initial location outside the portion of the catheter device that has not been entered into the patient's body as indicated by the solid position to the left of FIG. 1. After the fluid 8 has been tonometered or equilibrated with body gases, the catheter may be withdrawn while holding the sleeve stationary until the sleeve covers the chamber 7 as shown by dotted lines in the right of FIG. 1; or the sleeve may be moved downwardly immediately after withdrawal of the catheter device from the patient's body. When the catheter device with the tonometered liquid reaches the clinical blood gas analyzing apparatus a hypodermic needle 10 having a hub 11 is used to puncture the membrane 5 where it forms the chamber 7 and aspirate the tonometered liquid from that chamber into intake tube 12 of the gas analyzing equipment diagrammatically indicated by numeral 13 entered into the hub 11 of the needle for direct connection to the analyzing equipment inlet. In order to hasten the aspiration of the tonometered liquid into the analyzing apparatus another needle may be inserted through the wall of the chamber 7 at another location to allow air to replace the fluid as it is removed. The gas of the catheter fluid is then analyzed, thereby determining the gas tension in the tissue in which the catheter was implanted and equilibrated.

The embodiment of FIG. 5 comprises an alternative method of encasing the tonometered liquid within the chamber 7 of the catheter device described above. In this instance, a tubular container 14 having a closed end 15 and the other end open, and having a diameter greater than that of the above catheter device, with the omission of the sleeve 9 is provided to contain a quantity of mineral oil 16 to surround the catheter and cover the membrane 5 where it forms the aforesaid chamber 7. The open end of the container 14 is provided with a stopper 17 having an opening therethrough just sufficient to receive the catheter 1 and the membrane 5 there around, to contain the mineral oil which is impermeable to gas. The stopper 17 is also provided with a vent 18 there through to allow any air initially in the container 14 to be vented, the real requirement being coverage of the entire chamber 7 of the catheter device with mineral oil and thus protected from exposure to air. The aforesaid needle 10 will puncture the container 14 and enter into the chamber 7 of the catheter device in the manner above described for aspirating the tonometered liquid in the chamber 7.

In the event the structure of FIG. 5 is preferred to the use of the sleeve 9 of FIG. 1, then in packaging a stopper without a vent 18 would be utilized to keep all of the mineral oil from spilling out, and the container with the mineral oil and the stopper 17 would also be included in the package with the catheter device. It would not be desirable to package the catheter device already in the mineral oil, which would be messy to remove before inserting in the patient.

As to the dimensions of the catheter device itself there is rather a considerable latitude for variation. Of course, the catheter device should be small in diameter to reduce trauma to a minimum. Older analyzing instruments may require 0.25 ml. to 0.50 ml. of tonometered liquid for gas analysis. Current analyzing instruments require a volume of 0.075 ml. to make determinations of $P_O$ and $P_{CO}$. Slightly less volume is required if only one gas is measured, about 0.050 ml. of tonometerized liquid. For example, at present a satisfactory dimension for the parts would be a 1.90 mm. for the diameter of the catheter 1; a diameter 0.46 mm. for the diameter of the elongated element 3; a diameter of 2.00 mm. for the diameter of the membrane 5; and a length of 4 cm. for the liquid chamber 7. These dimensions achieve a chamber volume slightly in excess of 0.1 ml. well within the volume requirements for conventional blood gas analyzing instruments. That leaves a total outside diameter of 2.00 mm. for the catheter device alone exclusive of the shielding sleeve 9 or the mineral oil container 14 which shielding means do not enter the body of the patient. Should a newer instrument for analyzation be developed capable of utilizing a smaller volume of tonometered liquid the size of the catheter device could be reduced by reducing the diameters of the various parts or by reducing the length of the liquid chamber 7. Therefor, a volume of tonometered liquid for analysis would be satisfactory within a range of 0.025 to 0.50 ml. whereby older and current analyzing instruments as well as newer instruments could be used for analysis without excessive lengths and diameters of the catheter device itself to achieve the required volume of tonometered liquid.

In view of the foregoing it will be apparent that the present invention provides distinct advantages for measurements of tissue gases over procedures and apparatus known heretofore.

I claim:

1. A catheter device incorporating the diffusion membrane principle to obtain samples of gases from the tissue of a patient for use with analyzing apparatus wherein the improvement comprises:

a catheter device having a plugged lumen forming a solid proximal portion, a distal portion having a sealed chamber therein, a diffusion membrane permeable to gases but impermeable to liquids forming the outer wall of said chamber, and said chamber being filled with a chemically inert tonometering liquid for equilibration with body tissue gases and of sufficient volume for analysis by blood gas analyzing equipment available in most hospitals.

2. The catheter device of claim 1 wherein said solid proximal portion comprises a catheter terminating short of the distal end of the device and forming an end wall of said chamber, a rigid imperforate elongated element plugging the lumen of said catheter and extending therebeyond, and an imperforate plug in which said element terminates and which plug forms the other end wall of said chamber.

3. The catheter device of claim 1, wherein said chamber has a liquid volume within the range of 0.025 to 0.50 ml.

4. The catheter device of claim 1, wherein said solid proximal portion comprises a catheter with its lumen plugged, and said diffusion membrane is tubular and extends over at least the proximal portion of said catheter.

5. The catheter device of claim 1 wherein said device has an overall outside diameter of approximately 2.0 mm., any desirable length, a chamber length of approximately 4 cm., and a chamber volume of approximately 0.1 ml.

6. The catheter device of claim 1, including gas impermeable means for disposition over and to cover said diffusion membrane where it forms the outer wall of said chamber to protect the gas level of the tonometered fluid in said chamber while in transport from the patient to a laboratory analysis apparatus.

7. The catheter device of claim 1, wherein said diffusion membrane is tubular with one end extending over said solid proximal portion, and a closure tip of monofilament material secured to the other end of said membrane to form a distal end seal.

8. The catheter device of claim 2, including a monofilament closure tip secured to said diffusion membrane to provide a distal end seal outside said plug.

9. The catheter device of claim 6, wherein said gas impermeable means is a sleeve slidable over and off said diffusion membrane where it forms the outer wall of said chamber.

10. The catheter device of claim 6, wherein said gas impermeable means is a container for a gas impermeable liquid into which the catheter device is placed.

* * * * *

UNITED STATES PATENT AND TRADEMARK OFFICE
CERTIFICATE OF CORRECTION

PATENT NO. : 4,016,863
DATED : April 12, 1977
INVENTOR(S) : John W. Brantigan

It is certified that error appears in the above-identified patent and that said Letters Patent are hereby corrected as shown below:

Column 5, line 13, $P_O$ and $P_{CO}$ should read $P_{O_2}$ and $P_{CO_2}$.

Signed and Sealed this twenty-sixth Day of July 1977

[SEAL]

Attest:

RUTH C. MASON
*Attesting Officer*

C. MARSHALL DANN
*Commissioner of Patents and Trademarks*